United States Patent [19]
Tyndorf et al.

[11] Patent Number: 5,518,925
[45] Date of Patent: May 21, 1996

[54] CULTURE SLIDE ASSEMBLY

[76] Inventors: Tadeusz A. Tyndorf, 8 Sandpiper Dr., Manalapan, N.J. 07226; Timothy A. Stevens, 171 Main St., Apt. 57, Madison, N.J. 07940

[21] Appl. No.: 468,782

[22] Filed: Jun. 6, 1995

[51] Int. Cl.[6] ............................ G02B 21/34; G01N 21/01
[52] U.S. Cl. ........................ 435/305.2; 435/305.3; 435/305.4; 435/240.1; 435/243; 422/102
[58] Field of Search ...................... 422/102; 435/30, 435/40, 285, 297, 298, 288.3, 305.1, 305.2, 305.3, 305.4, 240.1, 243; 350/536; 359/398; 356/244

[56] References Cited

U.S. PATENT DOCUMENTS

| | | | |
|---|---|---|---|
| Re. 33,826 | 2/1992 | Mitchell | 359/398 |
| 3,141,547 | 7/1964 | Newby | 206/1 |
| 3,572,892 | 3/1971 | Metzgar et al. | 350/95 |
| 3,726,764 | 4/1973 | White | 195/127 |
| 3,726,767 | 4/1973 | White | 195/127 |
| 3,745,091 | 7/1973 | McCormick | 195/139 |
| 3,879,106 | 4/1975 | McCormick | 350/95 |
| 3,961,346 | 6/1976 | White | 356/244 |
| 4,039,247 | 8/1977 | Lawman et al. | 350/95 |
| 4,387,972 | 6/1983 | Valencia | 350/536 |
| 4,637,693 | 1/1987 | Mitchell | 350/536 |
| 4,715,911 | 12/1987 | Johansson et al. | 156/69 |
| 4,722,598 | 2/1988 | Ford | 350/536 |
| 4,974,952 | 12/1990 | Focht | 350/536 |
| 5,002,377 | 3/1991 | Battifora et al. | 350/535 |

*Primary Examiner*—David A. Redding
*Attorney, Agent, or Firm*—Nanette S. Thomas

[57] ABSTRACT

The present invention is a culture slide assembly having a base member, a cooperable receptacle removably attached to the base and means for separating the receptacle from the base. Preferably, the assembly may be used for carrying out biological reactions or growth therein, such as growing tissue or cell cultures.

17 Claims, 6 Drawing Sheets

CULTURE SLIDE ASSEMBLY

BACKGROUND OF THE INVENTION

1. Field of the Invention

This invention relates to an assembly and a method for using the assembly in cell culture production. In particular, the assembly comprises a receptacle, a slide and means for separating the receptacle from the slide.

2. Description of Related Art

It is frequently desirable in medical laboratory practice as well as in biological research to grow various bacteria, cells or tissues in particular media and then to examine the resulting growth. A particular use of this technique is in virology laboratories where host cells are grown and then used to detect viral activity.

Typical apparatus useful for carrying out biological reactions or growth, such as growing tissue cultures is described in U.S. Pat. No. 3,726,764. The apparatus in U.S. Pat. No. 3,726,764 is a chamber attached to a glass slide with a liquid-impermeable seal. A special tool is wedged into the seal to separate the chamber from the glass slide.

A common problem which has confronted users of typical apparatus as described in U.S. Pat. No. 3,726,764 is that a separate tool to remove the chamber from the slide is not convenient and in spite of the high level of skill and care in separating the chamber and the slide, the potential for not shattering the glass slide is not always assured, and therefore, contamination of the cells on the slide is also not assured.

With the increased emphasis on the efficacy of medical and research products, a need exists for an improved apparatus for effectively and efficiently carrying out cell culture production. The improved apparatus would better protect the person carrying out the procedure and would be comparatively simple and inexpensive to manufacture as compared to available devices.

SUMMARY OF THE INVENTION

The present invention is a culture slide apparatus for carrying out biological reactions or growth therein, such as growing tissue or cell cultures.

The apparatus preferably comprises a base member, a cooperable receptacle comprising a plurality of chambers, means for removably attaching the receptacle to the base member and means for separating the base member from the receptacle. Desirably, the apparatus further comprises a lid for covering the opening of the receptacle.

Preferably the receptacle comprises a forward section and a rearward section and sidewalls that extend from a top surface to a bottom surface, wherein the bottom surface is removably mated with the base member. Most preferably, the bottom surface of the receptacle is removably attached to the base member with a liquid-impermeable seal. Preferably the liquid-impermeable seal may be comprised of a silicon or acrylate based composition as well as organopolysiloxane elastomers. A means for separating the base member from the receptacle is most preferably a movable lever. Desirably the lever is attached adjacent to the rearward section of the receptacle. The lever may be used to provide appropriate force between the receptacle and the base member to separate them.

Most preferably, the base member is a microscope slide. The base member and receptacle are most preferable made of glass or plastic.

To carry out biological reactions or growths in the apparatus, a liquid tissue culture medium is placed into the receptacle that is in contact with the base member. The medium is incubated to allow the tissue culture to grow and to attach to the base member. The liquid medium is then removed from the receptacle, and the receptacle is removed from the base with assistance from the lever. The tissue culture growth on the base can then be treated as desired and microscopically examined. This apparatus is also useful as an anaerobic chamber or as a blood culture chamber for microbiological assays.

A feature of the invention is its ease of use, in that the receptacle is easily removable from the base by the lever without the need to have a separate tool to wedge between the receptacle and the slide and that detachment forces are substantially reduced. Another feature of the invention is that the assembly is substantially self-contained in that the lever is attached to the assembly. Also, since the apparatus may be made from optically clear plastic, it may be easily disposable. Furthermore, the apparatus of the present invention improves the methods for carrying out biological reactions on slides by maintaining the integrity of the biological reaction due to the means for separating the chamber from the base member.

DETAILED DESCRIPTION

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 1:
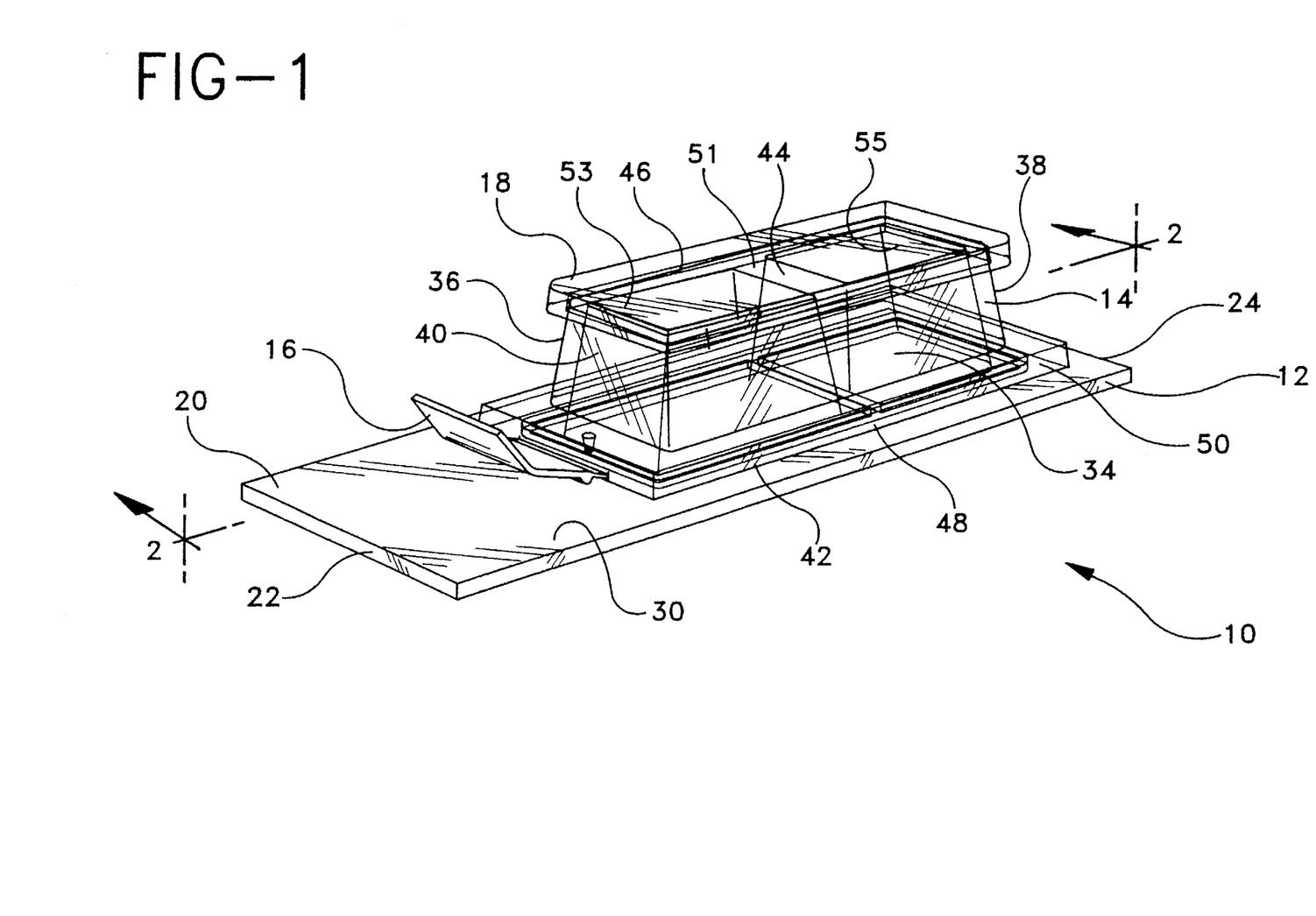
FIG. 1 is a perspective view of a culture slide apparatus.

The preferred apparatus of the present invention is illustrated in FIG. 1 wherein apparatus 10 comprises a base member 12, a receptacle 14, a lever 16 which is movable and a lid 18.

Base member 12 has a planar upper surface 20 and opposing ends 22 and 24 which are normal to surface 20. Upper surface 20 of base member 12 is flat to form a mating surface for receptacle 14. Base member 12 is preferably a microscope slide. Such microscope slide is preferably fabricated from soda glass which has been cleaned to remove oils, greases, surfactants, abrasives or other materials inhibitory to biological or bacterial growth. Alternatively, the microscope slide may be fabricated from plastic. Such plastic materials may include polystyrene and the like.

Receptacle 14 is located near end 24 and mates against surface 20 of base member 12 so as to leave a substantial portion 30 of surface 20 exposed near end face 22. This free surface area 30 can be etched so as to render it capable of receiving appropriate identification markings, such as an appropriate label.

Figure 2:
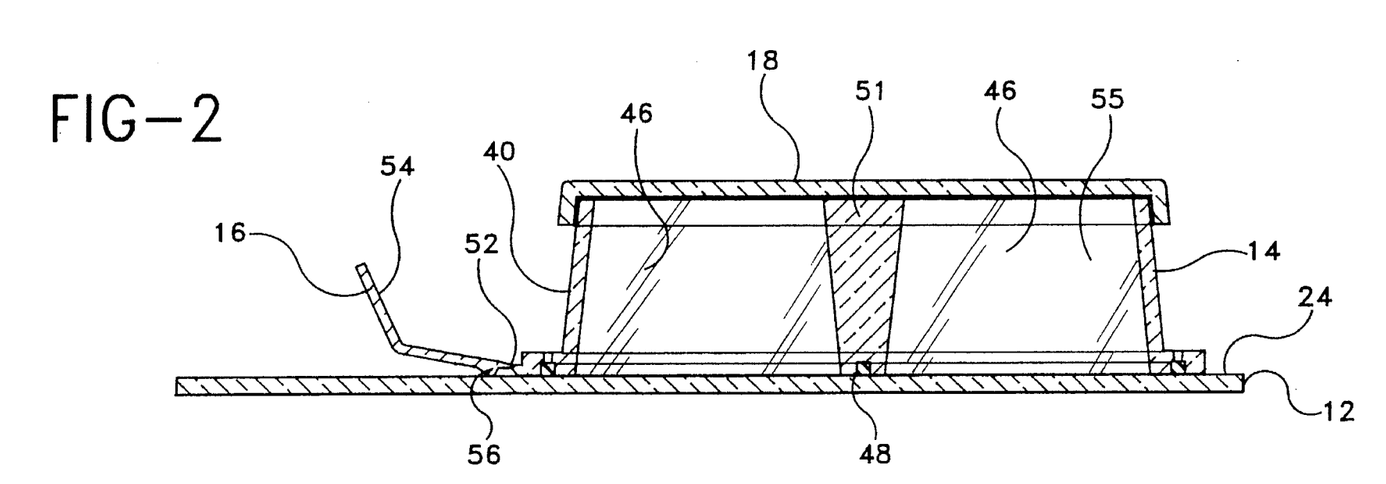
FIG. 2 is a cross-sectional side view of the culture slide apparatus of FIG. 1 taken along lines 2—2.

Receptacle 14 comprises opposing longitudinal sidewalls 34 and 36 and opposing transverse sidewalls 38 and 40 that define an open bottom 42 and an open top 44. The sidewalls extend from a top surface 46 to a bottom surface 48. At the bottom surface is a peripheral outwardly directed flange 50 surrounding bottom opening 42. Receptacle 14 further comprises a partition 51 that is parallel to and spaced equidistant from sidewalls 38 and 40 so as to form two chambers 53 and 55, As shown in FIG. 2 lever 16 comprises a rearward end 52, and a forward or working end 54. Rearward end 52 and forward end 54 of lever 16 meet at pivot position 56. Rearward end 52 is attached to flange 50 along sidewall 40 of receptacle 14. The lever is attached to the receptacle in such a way that it can be moved in a substantially vertical up or down direction.

As shown in FIG. 2, lid 18 is capable of fitting over and closing the open top of the receptacle and is easily removable.

Receptacle 14 is preferably formed from transparent polymer materials. Such materials include, but are not limited to, polystyrene, polypropylene, celluloid, polymethacrylate and polymethylmethacrylate, In the fabrication of the apparatus of the present invention, bottom surface 48 is removably attached to surface 20 of base member 12 near end face 24 by suitable means such as by an adhesive. Such adhesives include silicons or acrylates.

The principal criteria for a useful adhesive is that it provides desired removably adhesive characteristics between receptacle 14 and base 12, provides a liquid-impermeable seal, is substantially non-toxic to biological material subsequently employed in the apparatus, does not act as a source of growth for undesirable :microorganisms and reduces the amount of detachment forces required to separate the receptacle from the base.

Figure 3:
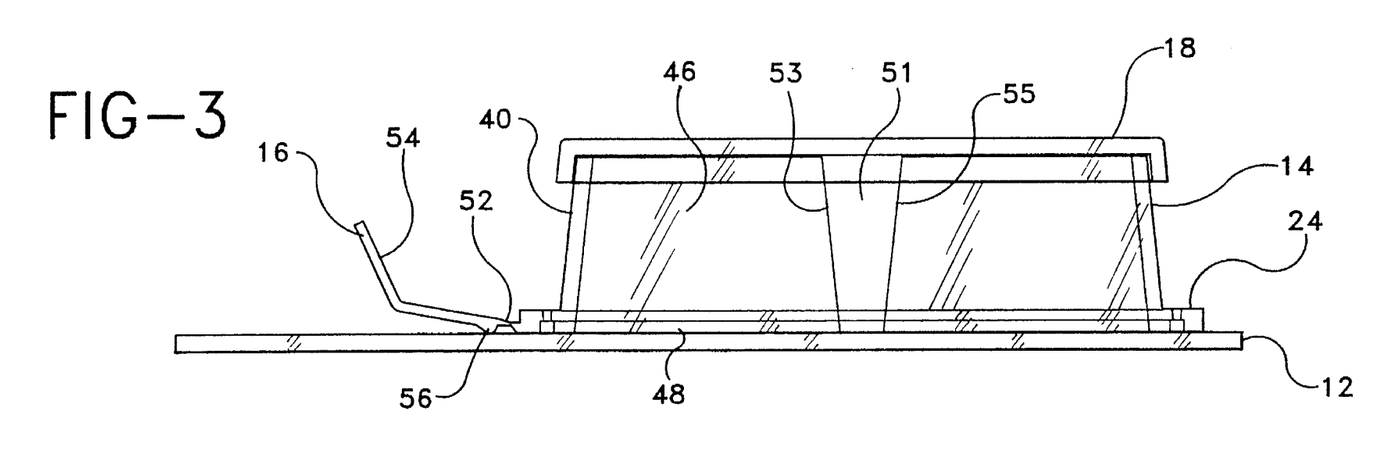
FIG. 3 is a side view of the culture slide assembly of FIG. 1 illustrating the movement of the lever.
Figure 4:
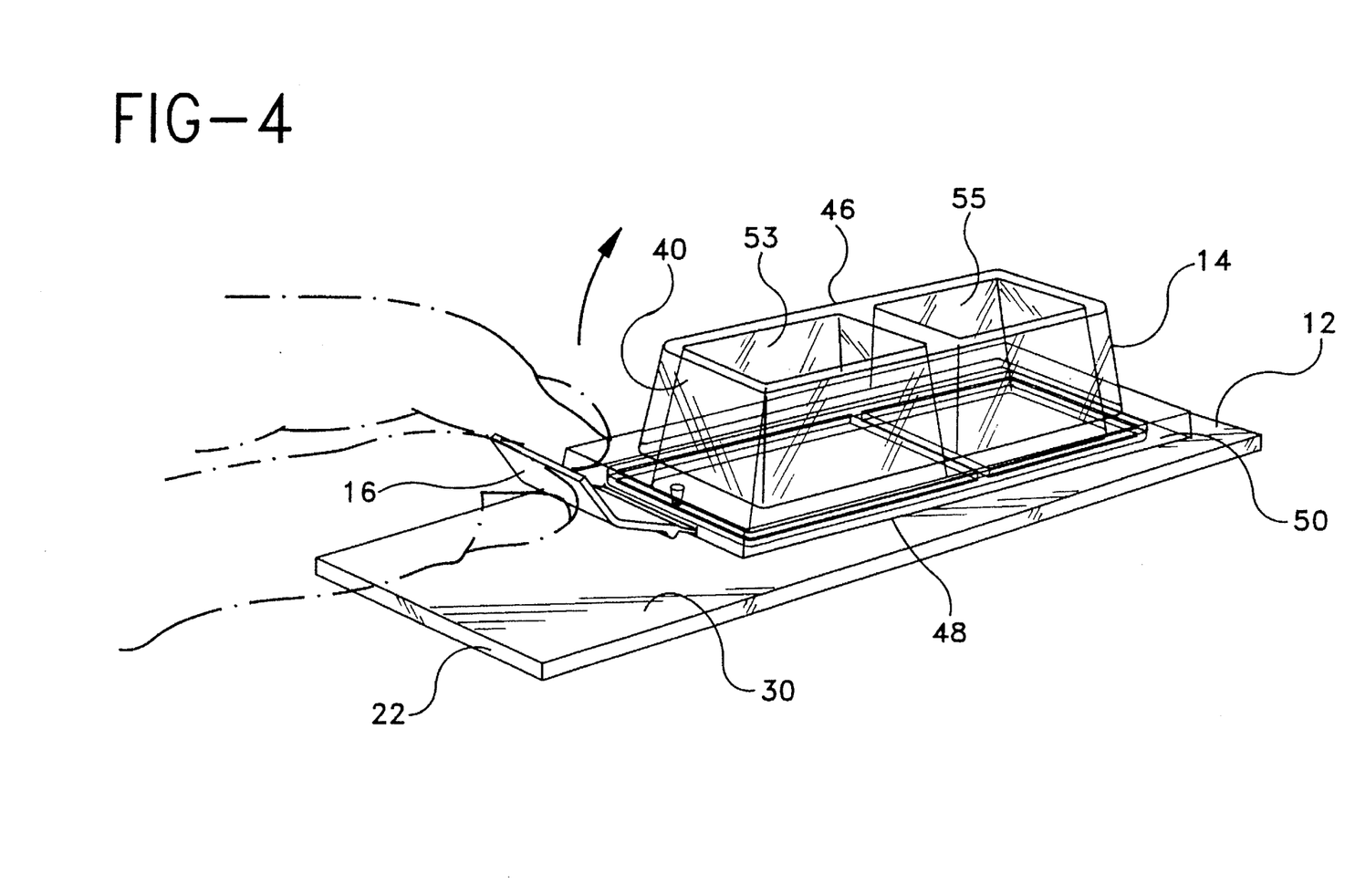
FIG. 4 illustrates the removal of the receptacle from the base member by the lever.

As shown in FIG. 3, the lever may be activated wherein manual force is applied to the working end toward the upper surface of the base so that the pivot position contacts the upper surface of the base. This motion allows the working end of the level to exert force on the flange and bottom surface of the chamber in an upward direction, so as to disengage the receptacle from the base. The receptacle may be removed from the base by using the lever as shown in FIG. 4.

Figure 5:
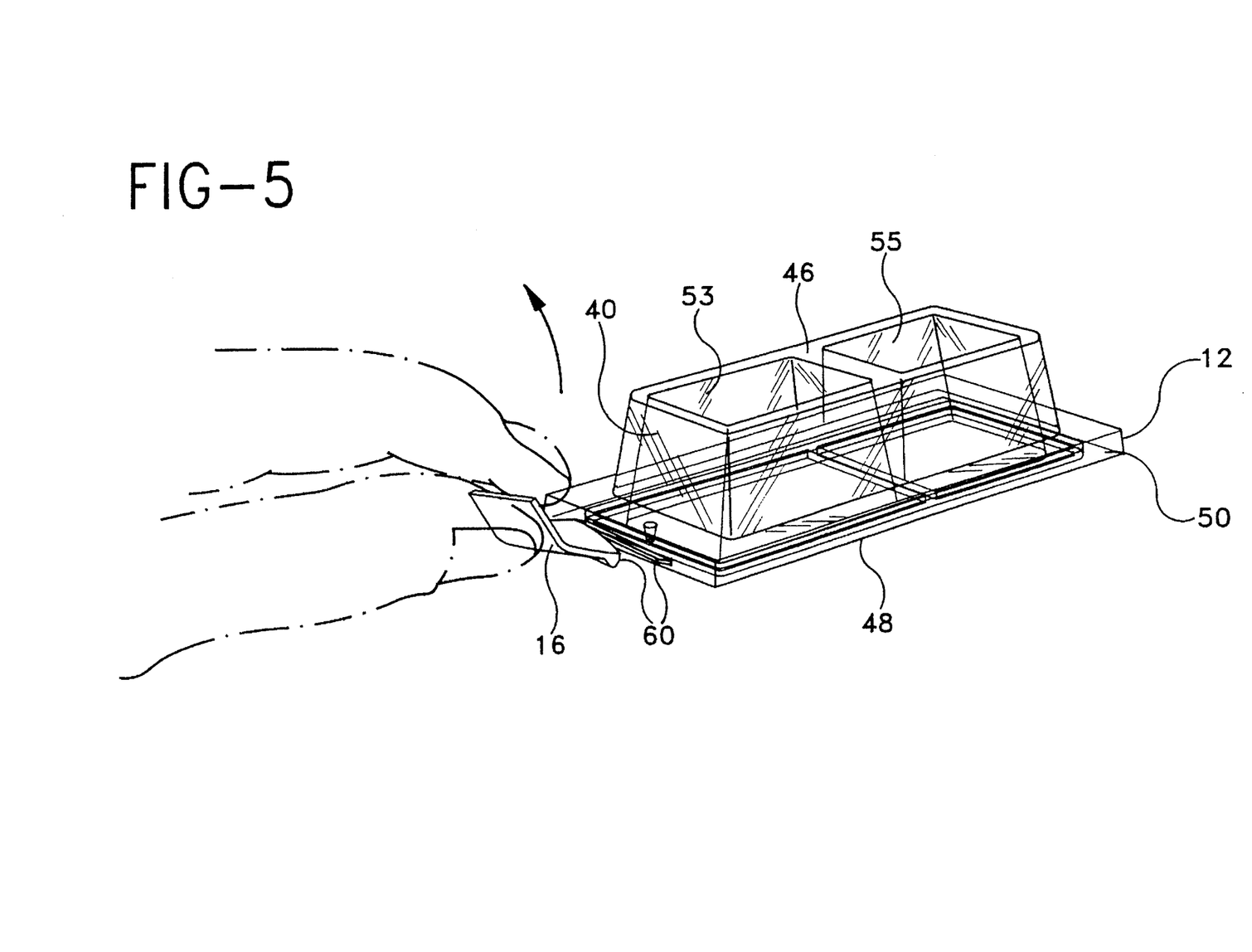
FIG. 5 illustrates the removal of the lever at the perforated edges.

Lever 16 may be made of plastic or other flexible material. Optionally, the lever may be removed from the receptacle at the perforated edges 60 between rearward end 52 and sidewall 40 of the receptacle as shown in FIG. 5.

The apparatus of the present invention may be employed in the following manner to grow for example tissue cultures. The lid is removed from the receptacle. The desired liquid tissue culture medium containing a suspension of cells to be grown is then placed into the receptacle. The apparatus is then placed in a suitable incubator and is incubated under well-known conditions to carry out the tissue culture growth. If desired, suitable treatment may be carried out on the cells and medium during this growth to achieve cytopathology changes in the cells. At the conclusion of the growth period a mass of tissue cells is attached to base. The tissue culture medium can then be removed from the chamber by aspiration. The receptacle is then removed from the base by applying manual force to the lever as shown in FIG. 3 and removing the receptacle as shown in FIG. 4. The mass of tissue cells attached to the base is then rinsed and fixed on the base, and the affixed tissue culture is then treated with an appropriate stain to stain the culture.

While the chamber described above has four-sides, it is understood that apparatus of the present invention can employ more or less sides as well as other geometric shapes, such as circular. Further, it is understood that the present invention can contain any desired number of chambers.

Figure 6:
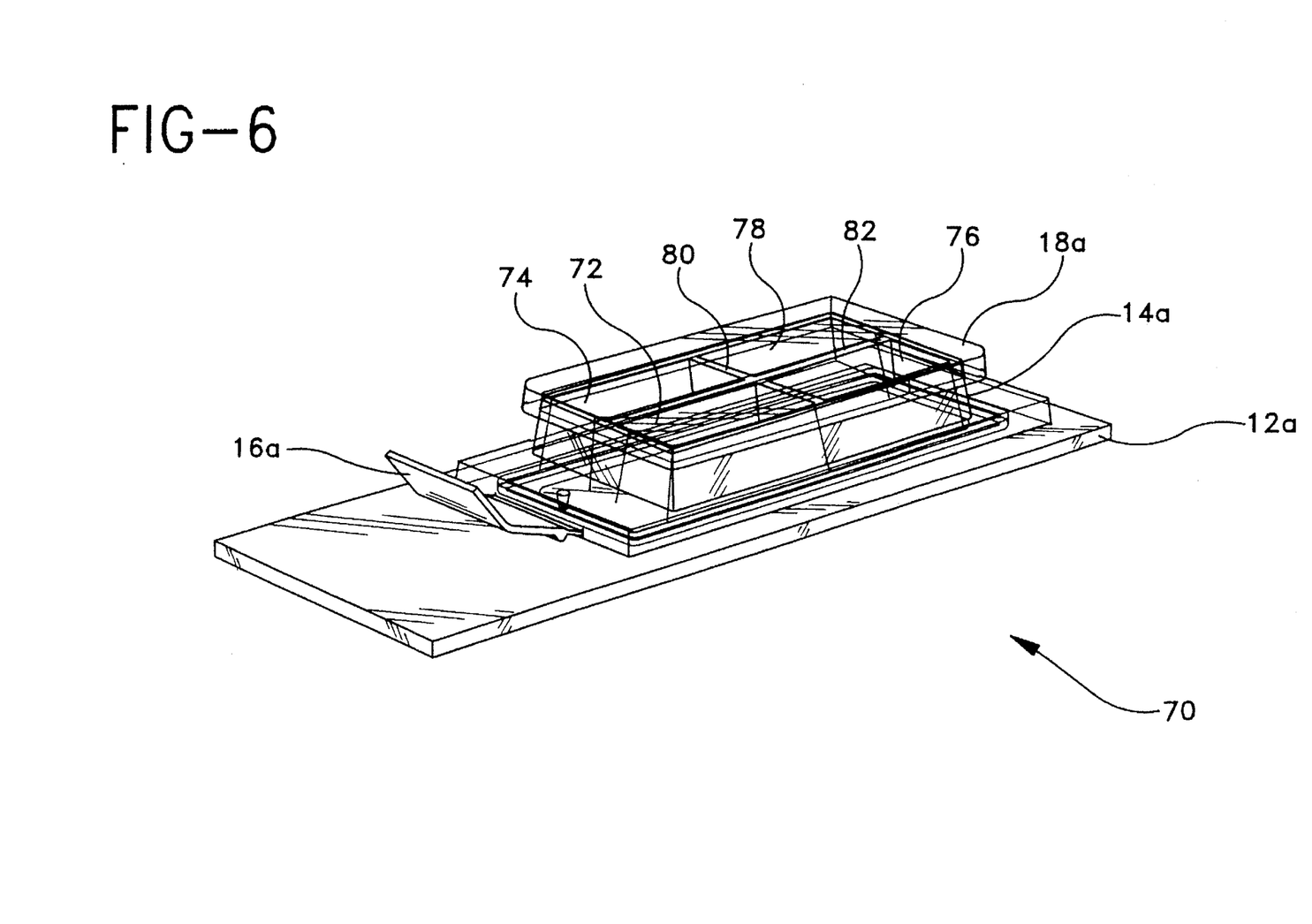
FIG. 6 is a perspective view of a four chamber culture slide apparatus, illustrating an additional embodiment of the invention.
Figure 7:
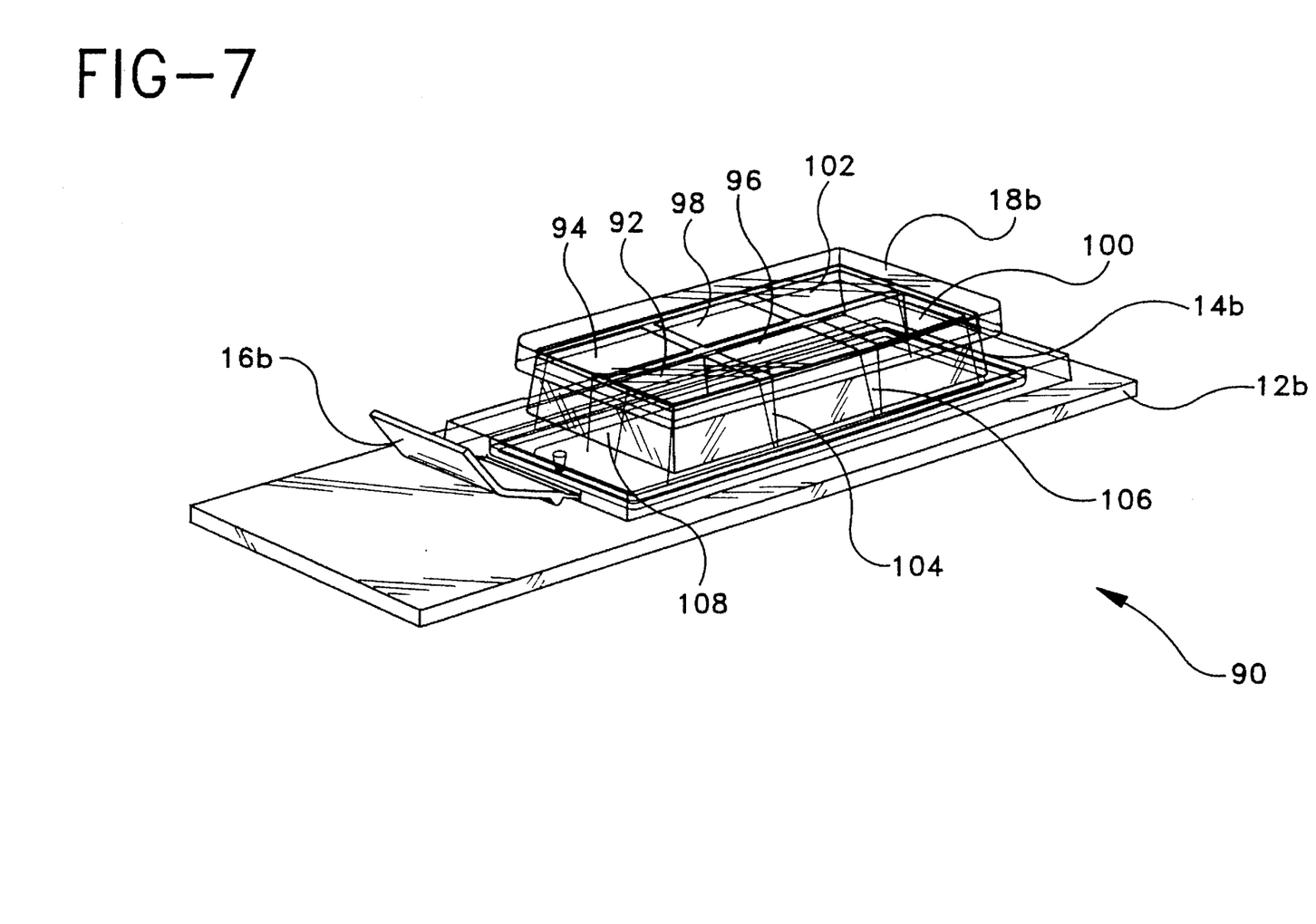
FIG. 7 is a perspective view of a six chamber culture slide apparatus, illustrating an additional embodiment of the invention.

FIGS. 6–7 are further embodiments of the invention that include many components which are substantially identical to the components of FIGS. 1–5. Accordingly, similar components performing similar functions will be numbered identically to those components of FIGS. 1–5, except that a suffix "a" will be used to identify those similar components in FIG. 6 and a suffix "b" will be used to identify those similar components in FIG. 7.

As illustrated in FIG. 6, a further embodiment of the invention includes a four chamber apparatus 70 having a base member 12a, a receptacle 14a, a lever 16a and a lid 18a. Receptacle 14a further includes four chambers 72, 74, 76 and 78 that are formed by partitions 80 and 82.

As illustrated in FIG. 7, a further embodiment of the invention includes a six chamber apparatus 90 having a base member 12b, a receptacle 14b, a lever 16b and a lid 18b. Receptacle 14b further includes six 92, 94, 96, 98, 100 and 102 that are formed by partitions 104, 106 and 108.

What is claimed is:

1. A culture slide apparatus comprising a base member, a receptacle comprising a plurality of chambers, means for removably attaching said receptacle to said base member and a movable lever attached to said chamber for separating said receptacle from said base member.

2. The apparatus of claim 1 wherein said means for removably attaching said receptacle to said base member is an adhesive material.

3. The apparatus of claim 2 wherein said adhesive provides a liquid-impermeable seal between said receptacle and said base member.

4. The apparatus of claim 1 wherein said base member comprises a planar upper surface and opposing ends which are normal to said surface.

5. The apparatus of claim 4 wherein said base member is a microscope slide.

6. The apparatus of claim 1 wherein said receptacle comprises top and bottom surfaces, forward and rearward sections and sidewalls that extend from said top surface to said bottom surface wherein said bottom surface is removably attached with said base member.

7. The apparatus of claim 1 wherein said lever comprises a rearward end and a forward end wherein said rearward and forward ends meet at a pivot position.

8. The apparatus of claim 7 wherein said lever is removably attached to said receptacle by perforated edges.

9. The apparatus of claim 1 further comprising a removable lid.

10. The apparatus of claim 1 wherein said receptacle comprises a top surface, a bottom surface and longitudinal sidewalls and opposing sidewalls that extend from said top surface to said bottom surface.

11. The apparatus of claim 10 wherein said receptacle comprises two chambers.

12. The apparatus of claim 10 wherein said receptacle comprises four chambers.

13. The apparatus of claim 10 wherein said receptacle comprises six chambers.

14. The apparatus of claim 10 further comprising a peripheral outwardly directed flange surrounding said bottom opening of said receptacle.

15. A method for growing tissue cultures with an apparatus having a base member, a receptacle comprising a plurality of chambers removably attached to said base member, a movable lever attached to said receptacle and a removable lid, comprising:

(a) placing a liquid tissue culture medium containing a suspension of cells in said chambers;

(b) placing said lid over said chambers;

(c) incubating said apparatus until a mass of tissue cells is attached to said base;

(d) removing said receptacle from said base with said lever;

(e) rinsing said tissue cells attached to said base;

(f) staining said tissue cells; and (g) examining said tissue cells.

16. The apparatus of claim 1 wherein said base member is glass or plastic.

17. The apparatus of claim 1 wherein said receptacle is plastic.

* * * * *

UNITED STATES PATENT AND TRADEMARK OFFICE
CERTIFICATE OF CORRECTION

PATENT NO : 5,518,925
DATED : May 21, 1996
INVENTOR(S): Tadeusz A. Tyndorf et al.

It is certified that error appears in the above-identified patent and that said Letters Patent is hereby corrected as shown below:

At Title page, first column, please add the following after [76] Inventors:

-- [73] Assignee: Becton, Dickinson and Company
Franklin Lakes, New Jersey --

Signed and Sealed this

Twenty-eighth Day of July, 1998

Attest:

BRUCE LEHMAN

*Attesting Officer*  *Commissioner of Patents and Trademarks*